(12) United States Patent
Czaplewski-Campbell et al.

(10) Patent No.: US 11,278,858 B2
(45) Date of Patent: Mar. 22, 2022

(54) MICROCAPSULES FOR TWO-STEP ANTICOUNTERFEITING

(71) Applicant: International Business Machines Corporation, Armonk, NY (US)

(72) Inventors: Sarah K. Czaplewski-Campbell, Rochester, MN (US); Jason T. Wertz, Pleasant Valley, NY (US); Eric J. Campbell, Rochester, MN (US); Brandon M. Kobilka, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 7 days.

(21) Appl. No.: 16/985,793

(22) Filed: Aug. 5, 2020

(65) Prior Publication Data

US 2022/0040657 A1 Feb. 10, 2022

(51) Int. Cl.
| | |
|---|---|
| *B01J 13/14* | (2006.01) |
| *C09K 11/07* | (2006.01) |
| *B41M 3/14* | (2006.01) |
| *B82Y 30/00* | (2011.01) |
| *B82Y 40/00* | (2011.01) |

(52) U.S. Cl.
CPC ............. *B01J 13/14* (2013.01); *B41M 3/144* (2013.01); *C09K 11/07* (2013.01); *B82Y 30/00* (2013.01); *B82Y 40/00* (2013.01); *C09K 2211/185* (2013.01)

(58) Field of Classification Search
CPC .... C09K 1/07; C09K 2211/185; B41M 3/144; B01J 13/14
See application file for complete search history.

(56) References Cited

U.S. PATENT DOCUMENTS

| | | | |
|---|---|---|---|
| 9,307,692 B2 | 4/2016 | Boday et al. | |
| 9,878,039 B1 | 1/2018 | King et al. | |
| 10,167,854 B2 | 1/2019 | Buvid et al. | |
| 10,357,921 B2* | 7/2019 | Campbell | C08G 59/68 |
| 10,392,452 B2 | 8/2019 | Campbell et al. | |
| 2015/0364710 A1 | 12/2015 | Chen et al. | |
| 2017/0129825 A1 | 5/2017 | Campbell et al. | |
| 2018/0046834 A1 | 2/2018 | Langerman et al. | |
| 2018/0265428 A1 | 9/2018 | Campbell et al. | |
| 2018/0327659 A1* | 11/2018 | Campbell | C08J 5/005 |
| 2018/0340850 A1 | 11/2018 | Campbell et al. | |

(Continued)

OTHER PUBLICATIONS

Zhang et al., "Synthesis and Application in Anticounterfeiting of RGB Upconversion Nanoparticles," Journal of Nanomaterials, vol. 2019, Article ID 3872591, Dec. 20, 2019, 7 pages.

(Continued)

*Primary Examiner* — C Melissa Koslow
(74) *Attorney, Agent, or Firm* — Kelsey M. Skodje

(57) ABSTRACT

A microcapsule, method, and article of manufacture are disclosed. The microcapsule includes an outer shell, a molecular sensitizer, a molecular annihilator, and an inner shell separating the molecular sensitizer from the molecular annihilator. The method includes forming microcapsules, each microcapsule having an outer shell, a molecular sensitizer, a molecular annihilator, and an inner shell separating the molecular sensitizer from the molecular annihilator. The article of manufacture includes at least one of the microcapsules.

20 Claims, 3 Drawing Sheets

(56) References Cited

U.S. PATENT DOCUMENTS

2018/0355126 A1 12/2018 Campbell et al.
2019/0118312 A1 4/2019 Bennett et al.
2019/0232439 A1 8/2019 Campbell et al.
2019/0309105 A1 10/2019 Campbell et al.
2020/0085949 A1 3/2020 King et al.

OTHER PUBLICATIONS

Baride et al., "Upconverting Nanomaterials for Security Applications," in C. Altavilla, ed., Upconverting Nanomaterials: Perspectives, Synthesis, and Applications. CRC Press, 2016, pp. 291-310.
Markon, "Counterfeit Prevention of Microelectronics through Covert Anti-Tamper Microcapsules." Ph.D. Dissertation, South Dakota School of Mines and Technology, 2013, 38 pages.
Xiong et al., "Towards Theranostic Multicompartment Microcapsules: in-situ Diagnostics and Laser-induced Treatment," Theranostics, 2013, vol. 3, Issue 3, pp. 141-151, Ivyspring International Publisher. DOI: 10.7150/thno.5846.
Tong et al., "Multilayer microcapsules with tailored structures for bio-related applications," Journal of Materials Chemistry, Aug. 2008, 18, pp. 3799-3812. DOI: 10.1039/b805717f.
Kreft et al., "Shell-in-Shell Microcapsules: A Novel Tool for Integrated, Spatially Confined Enzymatic Reactions," Angewandte Chemie International Edition, vol. 46, Issue 29, Feb. 2007, pp. 5605-5608. DOI: 10.1002/anie.200701173.

\* cited by examiner

MICROCAPSULES FOR TWO-STEP ANTICOUNTERFEITING

BACKGROUND

The present disclosure relates to anticounterfeit packaging and, more specifically, to microcapsules that emit visible light in response to a two-step authentication test.

Techniques for preventing the distribution of counterfeit products, such as microelectronics, include incorporating distinctive anti-counterfeiting elements into the products or their packaging. Markings that are difficult for counterfeiters to copy can be used to distinguish authentic items. For example, the surface of an authentic item can be labeled with a hologram, which can optionally have features such as high resolution and/or hidden elements (e.g., images that emerge when exposed to light at a defined angle and/or wavelength). Items can also be labeled with micro- or nanoscale letters, numbers, symbols, patterns, etc. Other types of anti-counterfeiting elements can include features that will show evidence of tampering. For example, an item can have a material such as an ink that is released or a fluorescent material that is removed when a counterfeiter attempts to sand off printed or engraved identifying information (e.g., serial number, manufacture date, brand name or logo, etc.) on an item.

SUMMARY

Various embodiments are directed to a microcapsule comprising an outer shell, a molecular sensitizer, a molecular annihilator, and an inner shell separating the molecular sensitizer from the molecular annihilator. The outer shell can include a transparent polymer. In some embodiments, the inner shell includes a polyelectrolyte crosslinked by photodimers. In other embodiments, the inner shell can include magnetic nanoparticles embedded in a polyelectrolyte multilayer. The molecular sensitizer can be palladium(II) octabutoxyphthalocyanine or platinum(II) tetraphenyltetranaphthoporphyrin. The molecular annihilator can be a furanyldiketopyrrolopyrrole or a perylene.

Additional embodiments are directed to a method of forming microcapsules. Each microcapsule includes an outer shell, a molecular sensitizer, a molecular annihilator, and an inner shell separating the molecular sensitizer from the molecular annihilator. The method can also include depositing the microcapsules on an object, rupturing the inner shell of the at least one of the microcapsules, and exposing the microcapsules to low-energy photons. In some embodiments, depositing the microcapsules includes arranging the microcapsules to form a pattern. The rupturing the inner shell can include exposing the microcapsules to ultraviolet light and/or a magnetic field. The method can also include evaluating visible light emitted from the microcapsules. In some embodiments, the inner shell includes a polyelectrolyte crosslinked by photodimers. In other embodiments, the inner shell can include magnetic nanoparticles embedded in a polyelectrolyte multilayer. The molecular annihilator can be a furanyldiketopyrrolopyrrole or a perylene. The molecular sensitizer can be palladium(II) octabutoxyphthalocyanine or platinum(II) tetraphenyltetranaphthoporphyrin.

Further embodiments are directed to an article of manufacture that includes at least one microcapsule. The microcapsule includes an outer shell, a molecular sensitizer, a molecular annihilator, and an inner shell separating the molecular sensitizer from the molecular annihilator. The article of manufacture can also include a protective cover positioned over the at least one microcapsule. In some embodiments, the inner shell includes a polyelectrolyte crosslinked by photodimers. In other embodiments, the inner shell can include magnetic nanoparticles embedded in a polyelectrolyte multilayer.

DETAILED DESCRIPTION

Figure 1A:
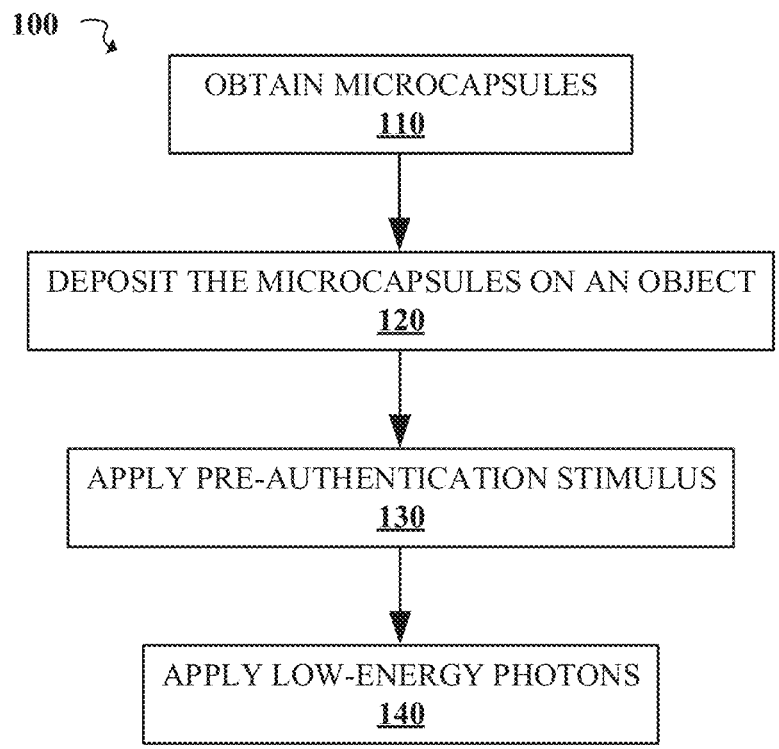
FIG. 1A is a flow diagram illustrating an authentication process, according to some embodiments of the present disclosure.

The production and sale of counterfeit products is a major concern in a wide variety of industries. For example, counterfeit microelectronics, pharmaceuticals, medical devices, food, and apparel can result in safety concerns, damage to a brand's reputation, and significant losses in sales of authentic items. In many cases, consumers are unaware that they are purchasing counterfeit products. However, anti-counterfeiting packaging and/or labeling can enable consumers, distributors, manufacturers, etc. to determine whether items they receive are authentic. Markings that are difficult for counterfeiters to copy can be used to distinguish authentic items. For example, the surface of an authentic item or its packaging can be labeled with a hologram, which can have features such as high resolution and/or hidden elements (e.g., images that emerge when exposed to light at a defined angle and/or wavelength). It can then be assumed that items lacking this hologram are counterfeits. However, when these markings are known to a counterfeiter, they can be added to counterfeit items as well.

Other types of anti-counterfeiting elements can include features that will show evidence of tampering. For example, an item can have a fluorescent material that is removed when a counterfeiter attempts to sand off printed or engraved identifying information (e.g., serial number, manufacture date, brand name or logo, etc.) on an item. A recipient of the item can then determine that tampering has occurred if the damaged area does not fluoresce under ultraviolet (UV) light. Additionally, items can have an ink that is released by sanding. However, these features can only be observed when damage has occurred.

Therefore, anti-counterfeiting features that are difficult to copy, and can be detected by a recipient without requiring surface damage, can offer advantages over existing techniques. The difficulty of copying an anti-counterfeiting feature can be increased when the feature cannot be detected without specific knowledge provided to its recipient by the item's manufacturer or distributor, separately from the item itself. Further, increasing the complexity and/or detail of hidden aspects of the anti-counterfeiting feature can provide additional levels of difficulty.

Disclosed herein are materials for anti-counterfeiting features that allow recipients of labeled items to carry out more than one step to determine the items' authenticity. The disclosed materials are multicompartment microcapsules containing molecular species for triplet fusion light upconversion. These species ("light upconversion molecules") include a sensitizer ([Sen]) and an annihilator ([An]). Sensitizer molecules absorb low-energy photons (e.g., photons from the infrared (IR), mid-IR, near-IR (NIR), or red region of the electromagnetic spectrum). When a [Sen] molecule absorbs a low-energy photon, it transitions from the ground state to a to singlet excited state ($^1$[Sen]*). Units of $^1$[Sen]* decay into triplet excited state species ($^3$[Sen]*), which transfer their energy to molecules of [An], resulting in formation of triplet excited state annihilator ($^3$[An]*) species. Pairs of $^3$[An*] then undergo triplet fusion, resulting in one of each pair transitioning to a higher energy singlet excited state ($^1$[An]*). Units of $^1$[An]* decay via fluorescence, emitting higher energy photons (e.g., visible light) than the low-energy photons initially absorbed by [Sen].

Because triplet fusion requires interaction between the sensitizer and annihilator species, it occurs when mixtures (e.g., solutions or suspensions) of [Sen] and [An] are exposed to low-energy photons. The multicompartment microcapsules disclosed herein keep solutions or suspensions of [Sen] and [An] separated into different compartments by a dividing component (e.g., a polymer shell) until a pre-authentication step occurs. This step causes the dividing component to rupture, allowing mixing of the [Sen] and [An] solutions/suspensions. When mixing has occurred, the microcapsules emit visible light upon exposure to low-energy photons in a subsequent authentication step.

FIG. 1A is a flow diagram illustrating an authentication process 100, according to some embodiments of the present disclosure. Multicompartment microcapsules containing light upconversion molecules are obtained. This is illustrated at operation 110. The multicompartment microcapsules include an outer shell encapsulating a first reactant and a second reactant, where the first reactant is isolated from the second reactant by a structure (e.g., an inner shell) that can rupture in response to a stimulus (e.g., UV light, a magnetic field, compression, heat, ultrasound, etc.). The outer shell is transparent. Herein, "transparent" refers to materials (e.g., shell polymers, core solvents, etc.) though which appropriate wavelengths of visible and NIR light can pass. Appropriate wavelengths include, at least, NIR light or other low-energy photons having sufficient energy to excite [Sen] to $^1$[Sen]* and wavelengths of light emitted by fluorescent decay of $^1$[An]* (e.g., visible light). In some embodiments, additional wavelengths (e.g., between about 100 nm-2500 nm and, optionally, wavelengths extending above and below this range) can pass through the transparent materials as well. It should be noted that, while the materials herein are described as transparent, translucent shell materials can be used in some embodiments.

The first and second reactants are light upconversion molecules selected so that each microcapsule contains a [Sen]/[An] pair capable of interacting to carry out triplet fusion light upconversion. Therefore, the first reactant can be a sensitizer and the second reactant can be an annihilator, or vice versa. In some embodiments, an annihilator is paired with a sensitizer where the energy of $^3$[Sen]* is slightly higher than that of $^3$[An]. However, any sensitizer where $^3$[Sen]* can transfer sufficient energy to excite [An] to $^3$[An] can be used. Additional factors that can be considered in choosing a [Sen]/[An] pair can include solubility, reactivity, efficiency, etc.

Figure 2:
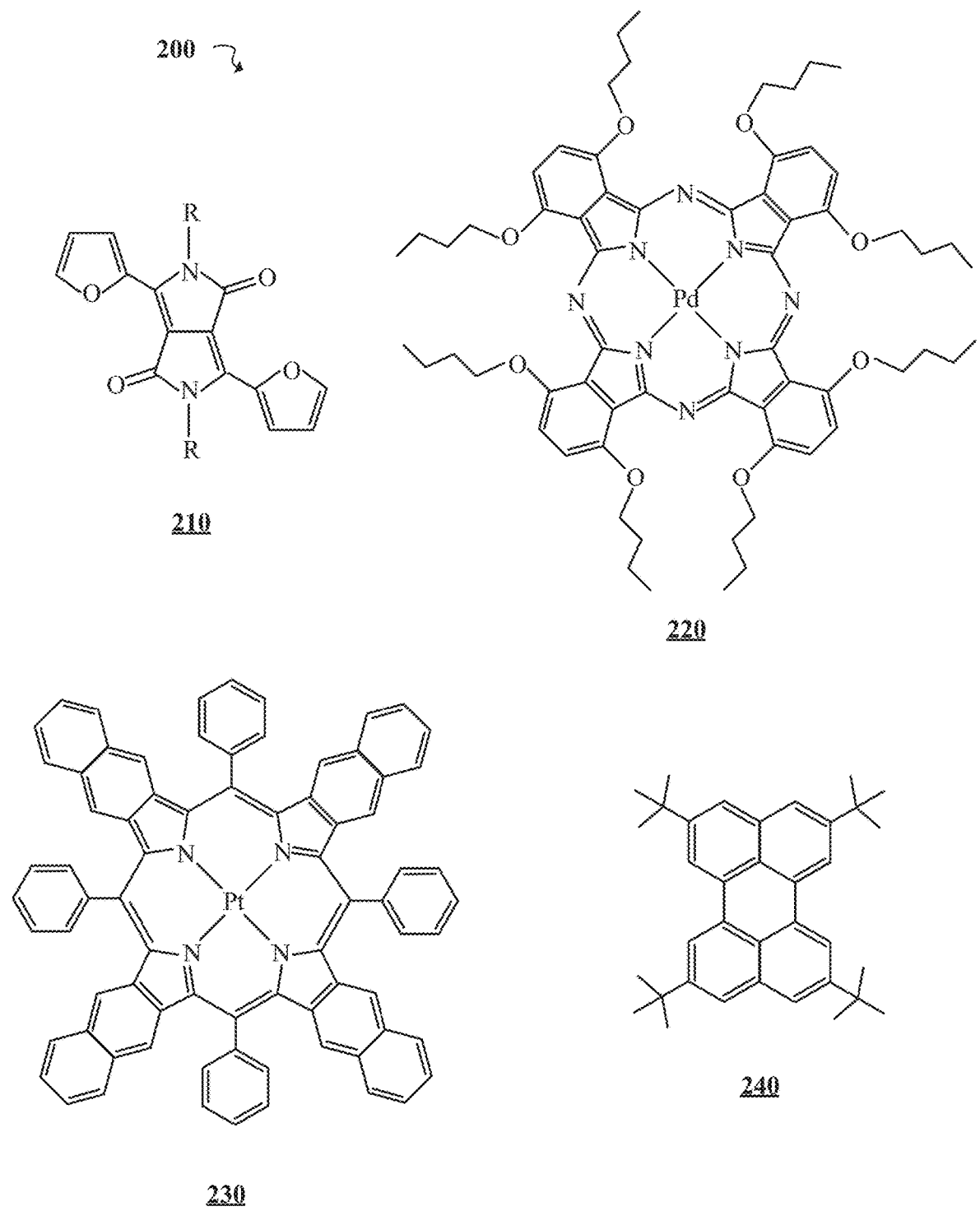
FIG. 2 is a chemical structure diagram illustrating examples of light upconversion molecules, according to some embodiments of the present disclosure.

In some embodiments, the sensitizer is a molecular compound having a high absorption coefficient in the NIR and/or red regions of the electromagnetic spectrum. In some embodiments, the sensitizer is a metal complex (e.g., a transition metal complex of a porphyrin or phthalocyanine). The annihilator can be an organic chromophore. In some embodiments, the annihilator is an organic compound having a high fluorescence quantum yield (e.g., about 0.9-0.95, 0.8-0.99, 0.6-1, etc.). Examples of light upconversion molecules that can be used are illustrated in FIG. 2.

Figure 1B:
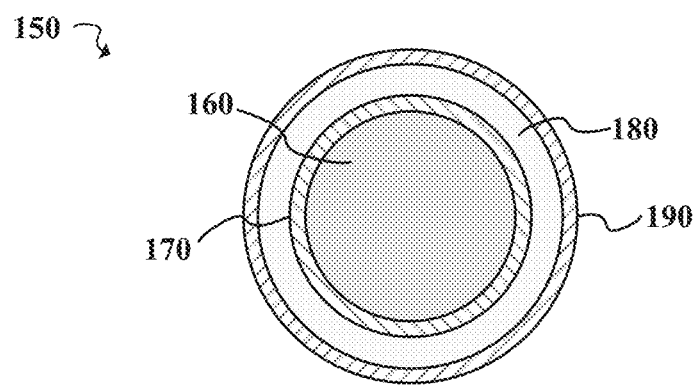
FIG. 1B is a schematic diagram illustrating a cross-sectional view of a shell-in-shell microcapsule, according to some embodiments of the present disclosure.
Figure 3:
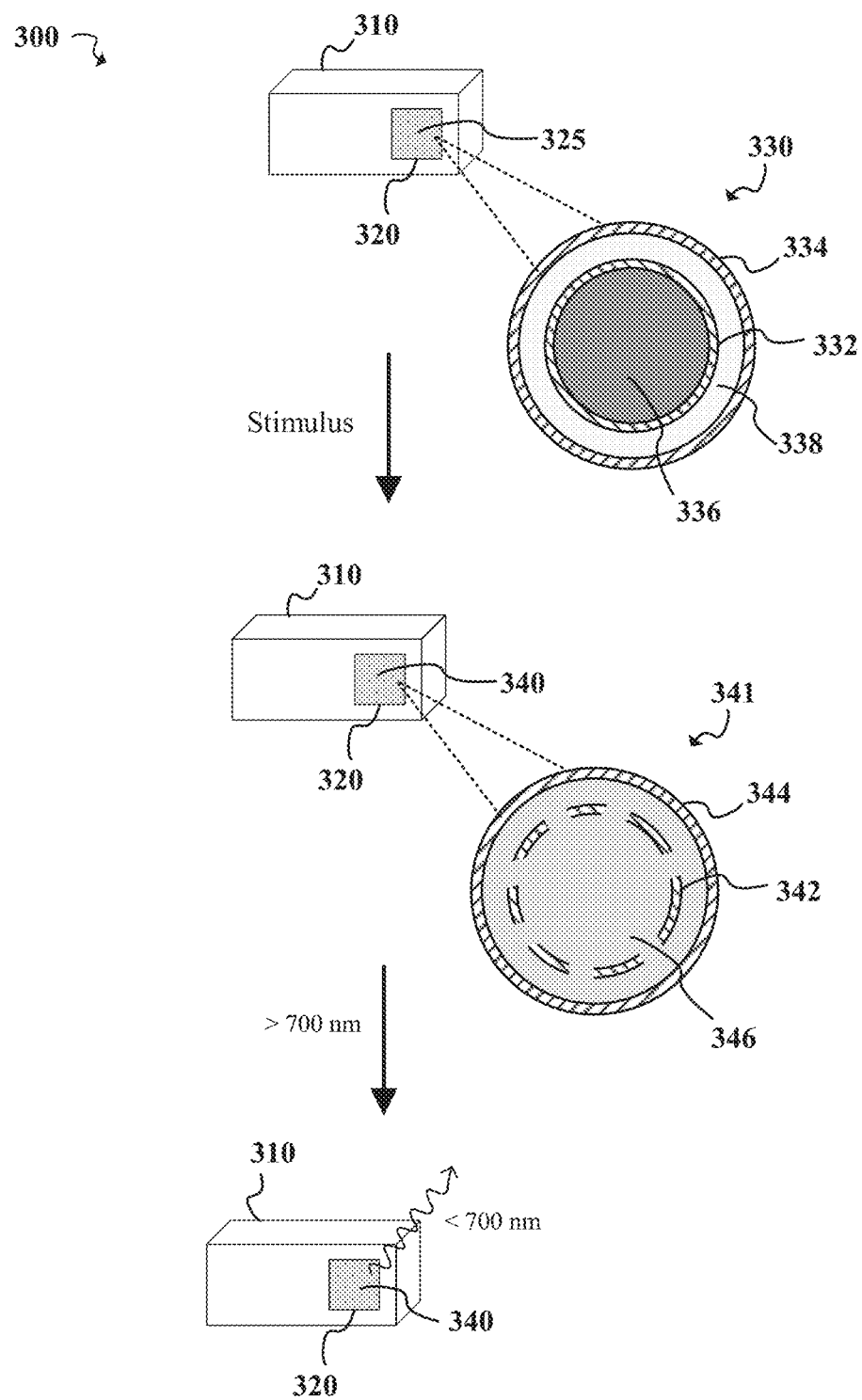
FIG. 3 is a schematic diagram illustrating a process of authenticating an object, according to some embodiments of the present disclosure.

The multicompartment microcapsules can have concentric ("shell-in-shell") structures, which include an inner shell and an outer shell. The inner shell encapsulates a solution or suspension of the first reactant. The inner shell encapsulating the first reactant is surrounded by a solution or suspension of the second reactant and the outer shell. Examples of shell-in-shell microcapsules are illustrated in FIGS. 1B and 3. However, in some embodiments, the light upconversion microcapsules can have at least two compartments in concentric, pericentric, innercentric, or acentric configurations.

The first and second reactants can be dissolved in a solvent or suspended in a transparent fluid (e.g., a solvent, an oil, etc.). Solvents that can be used to form a [Sen] or [An] solution can include aromatic solvents such as chlorobenzene (PhCl) and ethyl phenylacetate (EPA), non-aromatic solvents such as chloroform, and solvent mixtures such as trifluorotoluene/acetonitrile. In some embodiments, the same fluid is used for both reactants. However, any transparent fluids that do not react with the light upconversion molecules or shell materials, and are capable of mixing with one another when the inner shell has ruptured, can be used in some embodiments.

Various concentrations of first and second reactant solutions can be prepared. For example, upon mixing the two solutions, the concentration of [Sen] can range from approximately 0.003 mol %-0.18 mol %, and the concentration of [An] can range from approximately 3 mol %-10 mol %. However, other concentrations can be used. For example, the concentration of [Sen] can range from approximately 0.0001 mol %-0.003 mol %, and the concentration of [An] can range from approximately 0.18 mol %-3 mol % in some embodiments. The concentrations of [Sen] and [An] can vary depending upon solubility, wavelength of light for generating $^1$[Sen]*, absorption coefficient, etc.

The shell-in-shell microcapsules having light upconversion species can be prepared using techniques for forming shell-in-shell microcapsules known in the art. In some embodiments, the first reactant is immobilized in colloidal template particles via coprecipitation of the particle materials with the first reactant. The colloidal template particle material can be calcium carbonate ($CaCO_3$). In these instances, the first reactant can be coprecipitated with $Na_2CO_3$ and $CaCl_2$ [e.g., in an aqueous solution of about 1 M $Na_2CO_3$ and about 1 M $CaCl_2$). However, other colloidal template particles can be formed (e.g., polystyrene, silica ($SiO_2$), melamine formaldehyde, etc.). Magnetic nanoparticles (e.g., about 1-2% w/v magnetite or cobalt ferrite nanoparticles) can optionally be added to the colloidal template particle via coprecipitation as well. This is discussed in greater detail below.

Layer-by-layer assembly of oppositely charged polyelectrolytes can then be used to form shells (inner shells) around the colloidal template particles ("first reactant particles"). In some embodiments, the polyelectrolytes include the polyanion poly(sodium 4-styrenesulfonate) (PSS) and the polycation poly(allylamine hydrochloride) (PAH). However, other polyanions (e.g., poly(acrylic acid), poly(vinyl sulfonic acid), etc.) and polycations (e.g., poly(diallyl dimethyl ammonium chloride)) can be used. Further, the polyelectrolytes can be combined with crosslinkers, such as photodimers, photosensitive residues, and/or magnetic nanoparticles. This is discussed in greater detail with respect to step 130.

In the layer-by-layer assembly, the first reactant particles can be dispersed in a 0.5 M NaCl solution with about 2 mg/mL PSS, and shaken for about ten minutes to form PSS-coated first reactant particles. Excess PSS in solution can be removed by centrifugation followed by washing with deionized (DI) water. The PSS-coated first reactant particles can then be re-dispersed in a 0.5 M NaCl solution with about 2 mg/mL PAH, and shaken for about ten minutes to form first reactant particles coated in single polyelectrolyte (PSS/PAH) bilayers. Excess PAH can be removed by centrifugation and washing with DI water. Additional bilayers can be added by repeating the aforementioned steps. In some embodiments, five bilayers are deposited, but the number of bilayers can be varied depending on the desired thickness of the inner shell. The resulting coated first reactant particles are referred to herein as "inner-shell-encapsulated particles".

A colloidal layer immobilizing the second reactant can then be formed around the inner-shell-encapsulated particles in a second coprecipitation step. For example, the inner-shell-encapsulated particles can be suspended in an aqueous solution of $CaCl_2$, $Na_2CO_3$, and the second reactant. In other embodiments, different colloidal template materials can be used, such as materials for forming polystyrene, silica ($SiO_2$), or melamine formaldehyde. Mixing of the suspension (e.g., by agitation for about 20 seconds at room temperature) results in formation of inner-shell-encapsulated first reactant particles coated in colloidal template ($CaCO_3$) layers containing the immobilized second reactant, which are referred to herein as "ball-in-ball particles". The second coprecipitation step can also result in formation of second reactant colloidal particles as a side product. In instances where magnetic nanoparticles have been included in the first reactant particles, the ball-in-ball particles can be isolated from the second reactant colloidal particles by applying an external magnetic field to the suspension during at least one washing step.

Outer shells are then formed around the ball-in-ball particles. A variety of techniques can be used to form the outer shells. These can include techniques such as layer-by-layer assembly, oil phase separation, aqueous phase separation, interfacial polymerization, molecular encapsulation, in situ polymerization, pressing, piercing, powder bed methods, spray drying, spray freezing, air suspension, vacuum evaporation deposition, complex coacervation, long and short centrifugation, etc. The resulting outer shell is a transparent or translucent polymer shell (e.g., having a transmittance greater than about 90%). Examples of outer shell materials can include epoxy resin, polymethylmethacrylate or other acrylic resins, polyureas, polyurethane, poly(urea-formaldehyde), polyamides, polyolefins, polystyrenes, polyethers, polyethylene glycol, polyelectrolyte multilayers, alkyd resins, methyl cellulose, ethyl cellulose, carboxymethyl cellulose, hydroxyethyl cellulose, gelatin, gum arabic, shellac or other lac resins, mastic, sandarac, starches, dextrin, wax, rosin, sodium alginate, zein, etc.

When the ball-in-ball particles have been encapsulated in the outer shell, the template materials are extracted, leaving behind the first and second reactants, to produce the shell-in-shell microcapsules. For example, the $CaCO_3$ templates can be removed via complexation with ethylenediaminetetraacetic acid (EDTA). In these instances, the outer-shell-encapsulated ball-in-ball particles can be dispersed in an EDTA solution (e.g., about 0.2 M EDTA, pH 7.5), and shaken for several hours. The resulting EDTA calcium complex solution can then be removed by centrifugation. In some embodiments, this extraction process is repeated at least once. Removal of the template material yields shell-in-shell microcapsules having inner shells encapsulating a solution or suspension of the first reactant. The inner shells are surrounded by a solution or suspension of the second reactant, and the outer shell. In some embodiments, the diameters of the inner and outer shells can range from about 3 µm-5 µm and about 8 µm-10 µm, respectively. However, depending upon factors such as stir speed and reaction time, shell-in-shell microcapsules can have other sizes. For example, the diameters can range from about 0.5 µm-200 µm. The sizes can be tuned according to the planned application of the microcapsules.

The sizes of the light upconversion microcapsules can be controlled using a variety of known size control techniques during shell formation. Examples of these techniques include adjusting reaction parameters such as pH, temperature, stir speed, reaction time, solvent(s), concentration of reactants, etc. In some embodiments, the microcapsules have size distributions within the micron range (e.g., about 1 µm-10 µm, 10 µm-100 µm, 250 µm-500 µm, 100 µm-1000 µm). However, microcapsules of other sizes can be formed (e.g., about 10 nm-10 mm).

FIG. 1B is a schematic diagram illustrating a cross-sectional view of a shell-in-shell microcapsule 150 formed at operation 110 of process 100 (FIG. 1A), according to some embodiments of the present disclosure. The shell-in-shell microcapsule 150 includes a solution or suspension of a first reactant 160 encapsulated by an inner shell 170. The inner shell 170 is surrounded by a solution or suspension of a second reactant 180, which is encapsulated by an outer shell 190. In some embodiments, the first reactant 160 is a molecular sensitizer and the second reactant 180 is a molecular annihilator. In other embodiments, the first reactant 160 is a molecular annihilator and the second reactant 180 is a molecular sensitizer. The inner shell 170 can be a polyelectrolyte multilayer, and can optionally contain photosensitive species or magnetic nanoparticles. The outer shell 190 is a transparent or translucent polymer.

Referring again to FIG. 1A, the shell-in-shell microcapsules are deposited on the surface of an object. This is illustrated at operation 120. For example, the object can be an electronic device component or packaging for an electronic device. Examples of objects and surfaces are discussed in greater detail with respect to FIG. 3. Any appropriate techniques for microcapsule deposition can be used, such as printing, spraying, brushing on, and incorporation into a polymer or other coating deposited on the object. The microcapsules can be deposited in any shape/pattern (e.g., stripes, rectangles, alphanumeric characters, etc.), density, surface area, thickness, etc.

In some embodiments, the deposited shell-in-shell microcapsules each contain the same pairs of first and second reactants. In these instances, triplet fusion light upconversion in the deposited microcapsules will result in emission at the same wavelengths of visible light. However, a variety of different microcapsules can be formed at operation 120, wherein the different microcapsules include different sensitizers and/or annihilators. When the inner shell is ruptured (see below), this can result in the emission of different wavelengths of UV light generated by triplet fusion. That is, different [Sen]/[An] pairs can emit light of different colors. By tuning the [Sen]/[An] pairs in different batches of shell-in-shell microcapsules, multicolored patterns can be applied to an object surface.

For example, there can be a first batch of shell-in-shell microcapsules where the [Sen]/[An] pair can upconvert low-energy photons to yellow light (e.g., about 560 nm-590 nm), and a second batch of shell-in-shell microcapsules where the [Sen]/[An] pair can upconvert low-energy photons to blue light (e.g., about 450 nm-490 nm). Examples of sensitizers and annihilators such as these are illustrated in FIG. 2. Microcapsules from each batch can be deposited in different positions on an object to form a pattern that, after a pre-authentication step (see below), becomes visible upon irradiation with low-energy photons. For example, this pattern can be blue and yellow stripes, blue letters on a yellow background, a blue and yellow checkerboard pattern, etc.

A pre-authentication step is carried out. This is illustrated at operation 130. The pre-authentication step includes application of a first stimulus, which ruptures inner shells of the shell-in-shell microcapsules deposited on the object. Rupture of the inner shells allows the solutions or suspensions of the first and second reactants to mix. In some embodiments, the first stimulus is exposure to UV light (e.g., light at wavelengths below about 300 nm). In these instances, the microcapsules can have inner shell polymers that include photodimer repeat units and/or crosslinkers. In other embodiments, the first stimulus is exposure to a magnetic field. In these instances, the microcapsules can have magnetic nanoparticles embedded in their inner shells. In additional embodiments, the stimulus can be a compressive force or heat. This is discussed in greater detail below.

When the first stimulus is exposure to UV light, the inner shell polymer can be crosslinked by photodimers in some embodiments. In other embodiments, photodimers can be residues or copolymers in the inner shell polyelectrolyte layers. Further, inner shells may include both crosslinker and shell polymer repeat unit photodimers. Photodimers are dimers that undergo retro-dimerization upon exposure to UV light (e.g., wavelengths below about 240 nm-300 nm). Photodimers are formed by dimerization of monomers such as substituted or unsubstituted resveratrol, resorcinol, anthracene, etc. When the photodimers are resveratrol dimers, the inner shell photodimer (left) and its dissociated resveratrol monomers (right) can have the following structures:

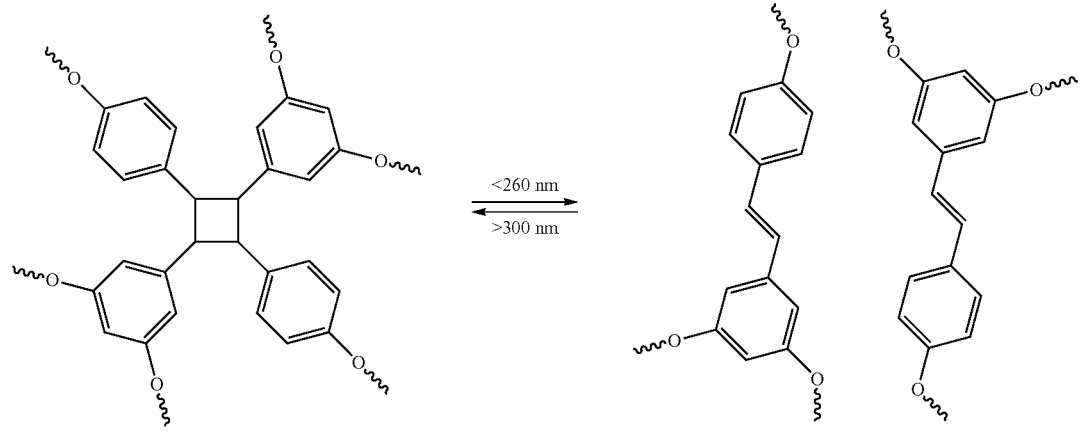

wherein the wavy lines represent bonds to the inner shell (e.g., crosslinking bonds). The resveratrol units remain dimerized in the absence of light at wavelengths less than about 300 nm. However, when shell-in-shell microcapsules containing these inner shell photodimers are exposed to UV light (e.g., having wavelengths shorter than about 260 nm), the dimerized resveratrol units dissociate, causing the inner shell to rupture.

While photodimers are illustrated herein, any appropriate photosensitive inner shell component can be used. Photosensitive components such as these can be compounds capable of dissociation upon UV light exposure. In some embodiments, triphenylmethane leucohydroxide residues can be incorporated into the inner shell. For example, the inner shell can be a polyelectrolyte shell (e.g., a poly(acrylic acid)-poly-ethylenimine complex) containing a copolymer of acrylic acid and bis[4-(dimethylamino)phenyl](4-vinylphenyl)methyl leucohydroxide. Upon exposure to UV light, the triphenylmethane leucohydroxide residues can dissociate into triphenylmethane cations and hydroxide anions. The dissociation can cause the inner shell to rupture.

In other embodiments, the inner shells can be ruptured by a magnetic field. For example, magnetic nanoparticles can be embedded in the inner shells. Examples of magnetic nanoparticles can include any appropriate nanoparticles made of a magnetic material (e.g., $Fe_3O_4$ (magnetite), cobalt ferrite, etc.). In some embodiments, the nanoparticles have diameters in the range of ~2 nm-5 nm, ~5 nm-10 nm, ~6 nm-25 nm, etc. The magnetic field can be applied to the shell-in-shell microcapsules by a magnetic field-generating device capable of providing a magnetic field with a strength and frequency sufficient for causing the magnetic nanoparticles to rotate and/or vibrate. The rotation/vibration of the magnetic nanoparticles causes the inner shell to rupture. In some embodiments, the magnetic field applied to the shell-in-shell microcapsules has a frequency of about 50 kHz-100 kHz and a strength of about 31 Oe. However, any magnetic field frequency and strength capable of causing the embedded nanoparticles to rotate and/or vibrate at a rate sufficient for rupturing the inner shell can be applied.

While a single pre-authentication step is illustrated herein, there can be more than one pre-authentication step in some embodiments. For example, there can be more than one batch of microcapsules applied to the object in a pattern, such as stripes. The microcapsules in one batch can have inner shells that rupture upon exposure to UV light, and the microcapsules in another batch can have inner shells that rupture upon exposure to a magnetic field. These microcapsules can optionally have different [Sen]/[An] pairs, thereby emitting two different colors of stripes upon rupturing both types of inner shells and irradiating with low-energy photons. In another example, the shell-in-shell microcapsules may have multilayered inner shells where each layer requires a different stimulus in order to rupture.

Authentication is confirmed by exposing the microcapsules to low-energy photons. This is illustrated at operation 140. Rupturing the inner shells in the pre-authentication at operation 130, and the ensuing solution or suspension mixing, enables the first and second reactants to come into close enough contact to carry out triplet fusion upconversion. The low-energy photons (e.g., wavelengths greater than about 700 nm) can be from a light source that emits red light, near-IR radiation, IR radiation, and/or far-IR radiation. In some embodiments, the light source can emit higher energy light (e.g., ~625 nm-700 nm, ~500-700 nm, etc.) in addition to the low-energy photons. If visible light is emitted from the microcapsules after exposure to low-energy photons, it can be determined that the object is authentic. However, in some embodiments the authenticity can be based on additional considerations, such as emitted light of a predetermined color, shape, and/or pattern. For example, an authentic object may have microcapsules that emit blue light. If exposure to low-energy photons causes the microcapsules to emit yellow light rather than blue, the object can be identified as a counterfeit.

FIG. 2 is a chemical structure diagram illustrating examples of light upconversion molecules 200, according to some embodiments of the present disclosure. Reactants 1 and 2 can be selected from these light upconversion molecules at step 110 of process 100 (FIG. 1A) in some embodiments. The illustrated compounds are a furanyldiketopyrrolopyrrole (FDPP) 210 having alkyl groups (e.g., methyl, ethyl, propyl, ethylhexyl, t-butyl, etc.) represented by R, palladium(II) octabutoxyphthalocyanine (PdPc(OBu)$_8$) 220, platinum(II) meso-tetraphenyltetranaphthoporphyrin (PtTPTNP) 230, and 2,5,8,11-tetra-tert-butylperylene (TTBP) 240. FDPP 210 and TTBP 240 are annihilators, and PdPc(OBu)$_8$ 220 and PtTPTNP 230 are sensitizers. Light emitted from selected [Sen]/[An] pairs of these molecules upon exposure to low-energy photons at operation 140 of process 100 can be used to determine an object's authenticity. PdPc(OBu)$_8$/FDPP system can upconvert low-energy photons to visible light of about 530 nm to 630 nm, and PtTPTNP/TTBP systems can upconvert NIR light to blue light (e.g., $\lambda_{max}$=450 nm).

In some embodiments, reactants 1 and 2 can be sensitizers and annihilators other than those illustrated in FIG. 2. Additional examples of annihilators that can be used in some embodiments can include rubrene (5,6,11,12-tetraphenylnapthacene), 9,10-diphenylanthracene, 9,10-bis(phenylethynyl)anthracene, 2,5-diphenyl oxazole, 9,10-disubstituted anthracenes, diketopyrrolopyrroles, perylenes, etc. Examples of sensitizers can include molecular compounds having high absorption coefficients in the NIR and/or red regions of the electromagnetic spectrum. However, any molecular compound capable of absorbing a photon and transferring triplet excitation energy to an annihilator can be selected. In some embodiments, the sensitizer is a transition metal (e.g., Pt, Pd, Zn, Cu, Co, Ru(CO), etc.) complex of a β- and/or meso-substituted porphyrin (e.g., 2-(3-[10,15,20-tris(3,5-di-tert-butylphenyl)porphyrin-5-yl]phenoxy)ethanol, octaethylporphyrin, tetrabenzoporphyrin, tetranaphthoporphyrin, tetraanthraporphyrin, tetraphenyltetrabenzoporphyrin, tetraphenyltetraanthraporphyrin, etc.). In addition to porphyrins, transition metal complexes of substituted or unsubstituted phthalocyanines (e.g., octabutoxyphthalocyanine, octa-triethyleneoxysulfonyl phthalocyanine, etc.) can be used.

Sensitizers can be selected based on factors such as excited state energy, lifetime of excited state, absorption coefficient in solution, solubility, etc. Examples of sensitizers can also include transition metal complexes of macrocyclic compounds such as naphthalocyanines, chlorins, and other cyclic tetrapyrroles. Further, sensitizers can include fused ring systems that include more than one porphyrin, phthalocyanine, and/or other macrocyclic compound. In some embodiments, sensitizers can be metal-free macrocyclic compounds such as porphyrins, phthalocyanines, naphthalocyanines, chlorins, etc., or organic dyes such as purpurin.

FIG. 3 is a schematic diagram illustrating a process 300 of authenticating an object 310, according to some embodiments of the present disclosure. This process 300 can be carried out according to techniques illustrated in FIG. 1A. The object 310 can be any item with a surface on which microcapsules can be deposited. Examples of object 310 surface materials can include plastics, metals, elastomers, silicones, polytetrafluoroethylene (PTFE), glass, and non-porous coatings on materials such as cardboard, wood, textiles, or ceramics. The object can be a housing for an electronic device, an internal component of an electronic device, a packaging material (e.g., a film, a rigid container, or a bag), a stick-on label, etc.

The object 310 includes an authentication area 320 on which is deposited shell-in-shell microcapsules 325. The surface of the authentication area 320 can be a different material than other object 310 components in some embodiments. The shapes and sizes of the authentication area 320 and object 310 are for illustrative purposes, and it should be understood that the authentication area 320 and object 310 can be any size or shape appropriate for their application. Further, the authentication area 320 and object 310 are not drawn to scale. The authentication area 320 can cover a greater or lesser portion of the object 310.

In some embodiments, there can be a protective layer (not shown) over the authentication area 320, such as a plastic film or cover, which can be removed prior to the authentication process 300. This protective layer can protect the microcapsules 325 from damage caused by excess light, moisture, abrasion, etc. In other embodiments, there is no protective layer. For example, the object 310 can be packaged in a container (e.g., a box), which can shield the microcapsules 325 from damage and/or light exposure. In some embodiments, the microcapsules 325 are shielded by both a protective layer and a package containing the object 310.

FIG. 3 also illustrates a cross-sectional view of a microcapsule 330 from the shell-in-shell microcapsules 325 deposited at the authentication area 320. The shell-in-shell microcapsule 330 has an inner shell 332 and an outer shell 334. The outer shell 334 and, optionally, the inner shell 332 are transparent. The outer shell 334 encapsulates solutions or suspensions of a first reactant 336 and a second reactant 338, which are separated from one another by the inner shell 332. In some embodiments, the shell-in-shell microcapsule 330 is substantially similar to the microcapsule 150 illustrated in FIG. 1B.

The first 336 and second reactants 338 are light upconversion molecules. If the first reactant 336 is a sensitizer, the second reactant 338 is an annihilator, and vice versa. For example, the first reactant 336 can be PdPc(OBu)$_8$ ([Sen]) and the second reactant 338 can be FDPP ([An]). In another example, the first reactant 336 can be TTBP ([An]) and the second reactant 338 can be PtTPTNP ([Sen]). In some embodiments, [Sen] and/or [An] are dissolved in a non-polar solvent such as PhCl or EPA. In some embodiments, [Sen] and/or [An] can be suspended in a liquid rather than being dissolved. Examples of molecular sensitizers and annihilators that can be the first 336 and second reactants 338 are discussed in greater detail with respect to FIG. 2.

The inner shell 332 can be a multilayered polyelectrolyte (e.g., PSS/PAH). In some embodiments, photodimers or other photosensitive species are incorporated into the inner shell 332 (e.g., as crosslinkers, comonomers, copolymers, etc.). In other embodiments, magnetic nanoparticles are incorporated into the inner shell 332. The outer shell 334 is a transparent or translucent polymer, such as a urea-formaldehyde polymer, an epoxy or acrylate resin, a polyurea, an alkyd resin, etc. Examples of inner 332 and outer shell 334 materials are discussed in greater detail with respect to FIG. 1A.

The authentication area 320 is exposed to a stimulus for pre-authentication. In some embodiments, the stimulus is UV light. In other embodiments, the stimulus is a magnetic field. The stimulus is applied in order to rupture inner shells (e.g., inner shell 332) of the shell-in-shell microcapsules 325, and therefore depends upon the composition of the inner shells. For example, UV light can be applied when the inner shells include photosensitive components, and a magnetic field can be applied when the inner shells include magnetic nanoparticles. In some embodiments, another type of stimulus can be used, such as a compressive force, ultrasound, heat, etc. In these instances, the outer shell can be made of a thicker or sturdier material than the inner shell. The thickness of the shell can be tuned by increasing or decreasing the number of polyelectrolyte bilayers formed in layer-by-layer assembly of the inner and/or outer shells.

Exposure to the pre-authentication stimulus yields microcapsules 340 with ruptured inner shells at the application area 320. FIG. 3 illustrates a cross-sectional view of one 341 of these microcapsules 340. This example microcapsule 341 has a ruptured inner shell 342 and an intact outer shell 344. The outer shell 344 encapsulates a solution or suspension of a [Sen]/[An] mixture 346. The [Sen]/[An] mixture 346 forms because the ruptured inner shell 342 allows mixing of the solutions or suspensions of the first 336 and second reactants 338.

The microcapsules 340 are then exposed to low-energy photons (e.g., wavelengths greater than about 700 nm) from a light source (not shown). In some embodiments, the light source can also emit higher energy light (e.g., visible, UV, etc.). The low-energy photons are absorbed and upconverted by the light upconversion molecules in the microcapsules 340. The resulting higher energy photons are emitted from the microcapsules 340. These higher energy photons are represented by a wavy arrow in FIG. 3. When the higher energy photons have wavelengths in the visible region of the EM spectrum, authenticity of the object may be determined by eye. However, light detectors can optionally be used to determine whether the correct wavelength(s) of light are emitted.

In some embodiments, compounds disclosed herein can have additional moieties such as epoxides, hydroxyl, propylene carbonate, alkyl halides, esters, alkynes, amines, isocyanates, acid chlorides, chloroformates, thiols, oxiranes, silyls, carboxylic acids, alkoxyls, alkyls, etc. Herein, "alkyl" refers to $C_1$-$C_{100}$ radicals, which can be linear, branched, or cyclic. Examples of alkyl groups can include methyl, ethyl, n-propyl, iso-propyl, n-butyl, iso-butyl, sec-butyl, tert-butyl, pentyl, hexyl, octyl, cyclopropyl, cyclobutyl, cyclopentyl, cyclohexyl, and cyclooctyl. In some embodiments, the alkyls are unsaturated (e.g., alkenes and alkynes).

The compounds described herein can contain one or more chiral centers. Unless otherwise noted, the disclosed structures cover all stereoisomers, conformers, rotamers, isomers, and enantiomers of the represented compounds. Further, polymers or other materials containing the disclosed compounds can include racemic forms of the compounds in addition to individual stereoisomers, as well as mixtures containing any of these. Substituents on the compounds described herein may participate in additional chemical reactions, transformations, or interactions, which can include synthesis, decomposition, single and/or double replacement, oxidation/reduction, acid/base, nucleophilic, electrophilic and radical substitutions, addition/elimination reactions, crosslinking reactions, and polymerization reactions.

Where isomers of a named alkyl, alkenyl, alkoxy, aryl, or other functional group exist (e.g., n-butyl, iso-butyl, sec-butyl, and tert-butyl), reference to a member of the group without specifying a particular isomer (e.g., butyl) is intended to include all isomers in the family (e.g., n-butyl, iso-butyl, sec-butyl, and tert-butyl). Further, unless specified otherwise, reference to one member of the group (e.g., n-butyl) includes the remaining isomers in the family (e.g., iso-butyl, sec-butyl, and tert-butyl).

Unless otherwise noted, chemical reactions are performed at ambient conditions or under slight heating with no special atmosphere or head space, and may be performed using standard organic solvents to manage mix properties such as viscosity and flow index. Standard procedures for quenching reactions, solvent removal, and purification are performed. Room temperature is between about 15° C. and 30° C. unless otherwise indicated. Ranges (e.g., time, concentration, temperature, etc.) indicated herein include both endpoints and all numbers between the endpoints. Unless specified otherwise, the use of "about," "approximately," or a tilde (~) in connection with a range applies to both ends of the range (e.g., "approximately 1 g-5 g" should be interpreted as "approximately 1 g-approximately 5 g"), and in connection with a list of ranges applies to each range in the list (e.g., "about 1 g-5 g, 5 g-10 g, etc." should be interpreted as "about 1 g-about 5 g, about 5 g-about 10 g, etc."). Unless otherwise indicated, modifying terms such as "about," "approximately," and "~" indicate +/−10% of a recited value, range of values, or endpoints of one or more ranges of values.

The processes discussed herein, and their accompanying drawings, are not to be construed as limiting. One skilled in the art would recognize that a variety of techniques may be used that vary in conditions, components, methods, etc., which ultimately generate light upconversion microcapsules. In addition, the conditions can optionally be changed over the course of a process. Further, in some embodiments processes can be added, omitted, or carried out in alternate orders, while still remaining within the scope of the disclosure, as will be understood by a person of ordinary skill in the art. It should also be noted that processes can be carried out by a single entity, or by multiple entities. For example, a first entity may prepare the multicompartment microcapsules, a second entity may deposit the microcapsules on an object, and a third entity may carry out the authentication steps.

What is claimed is:

1. A microcapsule, comprising:
    an outer shell;
    molecular species for triplet-fusion light upconversion, the molecular species comprising:
        a molecular sensitizer; and
        a molecular annihilator; and
    an inner shell separating the molecular sensitizer from the molecular annihilator.

2. The microcapsule of claim 1, wherein the outer shell comprises a transparent polymer.

3. The microcapsule of claim 1, wherein the inner shell comprises a polyelectrolyte crosslinked by photodimers.

4. The microcapsule of claim 1, wherein the inner shell comprises magnetic nanoparticles embedded in a polyelectrolyte multilayer.

5. The microcapsule of claim 1, wherein the molecular sensitizer is selected from the group consisting of palladium (II) octabutoxyphthalocyanine and platinum(II) tetraphenyltetranaphthoporphyrin.

6. The microcapsule of claim 1, wherein the molecular annihilator is selected from the group consisting of a furanyldiketopyrrolopyrrole and a perylene.

7. A method, comprising:
    obtaining microcapsules, each of the microcapsules comprising:
        an outer shell;
        molecular species for triplet-fusion light upconversion, the molecular species comprising:
            a molecular sensitizer; and
            a molecular annihilator; and
        an inner shell separating the molecular sensitizer from the molecular annihilator.

8. The method of claim 7, further comprising:
    depositing the microcapsules on an object;
    rupturing the inner shell of at least one of the microcapsules; and
    exposing the microcapsules to low-energy photons.

9. The method of claim 8, wherein the depositing the microcapsules on the object comprises arranging the microcapsules to form a pattern.

10. The method of claim 8, wherein the rupturing the inner shell of the at least one of the microcapsules comprises exposing the microcapsules to ultraviolet light.

11. The method of claim 8, wherein the rupturing the inner shell of the at least one of the microcapsules comprises exposing the microcapsules to a magnetic field.

12. The method of claim 8, further comprising evaluating visible light emitted from the microcapsules.

13. The method of claim 7, wherein the inner shell comprises a polyelectrolyte crosslinked by photodimers.

14. The method of claim 7, wherein the inner shell comprises magnetic nanoparticles embedded in a polyelectrolyte multilayer.

15. The method of claim 7, wherein the molecular annihilator is selected from the group consisting of a furanyldiketopyrrolopyrrole and a perylene.

16. The method of claim 7, wherein the molecular sensitizer is selected from the group consisting of palladium(II) octabutoxyphthalocyanine and platinum(II) tetraphenyltetranaphthoporphyrin.

17. An article of manufacture, comprising:
    at least one microcapsule, comprising:
        an outer shell;
        molecular species for triplet-fusion light upconversion, the molecular species comprising:
            a molecular sensitizer; and
            a molecular annihilator; and
        an inner shell separating the molecular sensitizer from the molecular annihilator.

18. The article of manufacture of claim 17, further comprising a protective cover positioned over the at least one microcapsule.

19. The article of manufacture of claim 17, wherein the inner shell comprises a polyelectrolyte crosslinked by photodimers.

20. The article of manufacture of claim 17, wherein the inner shell comprises magnetic nanoparticles embedded in a polyelectrolyte multilayer.

* * * * *